United States Patent [19]

Matsushita et al.

[11] 4,362,386
[45] Dec. 7, 1982

[54] METHOD AND APPARATUS FOR RECOGNIZING SMEARS

[75] Inventors: Hajime Matsushita; Yoshimasa Shimura, both of Katsuta, Japan

[73] Assignee: Hitachi, Ltd., Tokyo, Japan

[21] Appl. No.: 208,076

[22] Filed: Nov. 18, 1980

[30] Foreign Application Priority Data

Nov. 19, 1979 [JP] Japan .............................. 54-148912

[51] Int. Cl.³ .......................................... G01N 33/48
[52] U.S. Cl. .................. 356/39; 235/92 PC
[58] Field of Search ............... 356/39, 71; 235/92 PC, 235/146.3 CA

[56] References Cited

U.S. PATENT DOCUMENTS 3,827,804 8/1974 Miller et al. .......................... 356/39
4,175,859 11/1979 Hashizume et al. .................. 356/39

OTHER PUBLICATIONS

"Leukocyte Pattern Recognition", Bacus et al., IEEE Transactions of Systems, Man, & Cybernetics, vol. SMC 2, No. 4, Sep. 1972, pp. 513-526.

Primary Examiner—Vincent P. McGraw
Attorney, Agent, or Firm—Antonelli, Terry & Wands

[57] ABSTRACT

After a slide glass having blood smeared thereon has been mounted on a movable stage of a microscope, the stage is moved to position a view field of the microscope to the center of the slide glass. Then, the stage is moved in one direction along the length of the slide glass. The view field of the microscope moves as the stage is moved so that red blood corpuscle densities on the smear are measured sequentially along the length of the slide glass. Based on the measurement a computer determines an optimum test area on the smear for the recognition of white blood corpuscles and the stage is moved to a start position of the optimum test area by an instruction from the computer. Thereafter, a normal stage scan operation for detecting the white blood corpuscles is carried out and the detected white blood corpuscles are automatically classified.

10 Claims, 11 Drawing Figures

METHOD AND APPARATUS FOR RECOGNIZING SMEARS

BACKGROUND OF THE INVENTION

The present invention relates to a method and an apparatus for recognizing a smear, and more particularly to a method and an apparatus for automatically recognizing an object smeared in test samples on a slide.

In a prior art method for examining blood cells, it has been common that a skilled examiner visually observes a blood sample smeared on a slide glass by an optical microscope to discover white blood corpuscles and classify them by pattern recognition technique in accordance with shapes and colors of the white blood corpuscles. However, since such a visual method accompanies with the fatigue of the examiner, a long time work is difficult to do and only a small number of samples can be processed. In order to resolve such a problem, an automatic classifying apparatus for white blood corpuscles has been developed. Apparatus for classifying the blood smeared on a slide and observed by a microscope in accordance with the configuration of the blood cells are shown in the U.S. Pat. No. 4,175,859 to A. Hashizume et al, U.S. Pat. No. 3,827,804 to M. N. Miller et al and an article entitled "Leubocyte Pattern Recognition" by J. W. Bacus et al, IEEE Transactions on Systems, Man and Cybernetics, Vol. SMC-2, No. 4, page 513, 1972.

Blood smears to be tested usually have various blood cell distribution densities and conditions on a slide gears depending on the smear condition and it is difficult to prepare samples of a uniform blood cell distribution.

Particularly when the samples are prepared by hand application or an automatic wedge type smear apparatus, the configuration of the blood cell changes from position to position on the slide glass. Accordingly, when such a sample is to be tested, an examiner views each sample through a microscope to find out an area of less change in configuration before the blood cells are automatically classified by the apparatus.

SUMMARY OF THE INVENTION

It is an object of the present invention to provide a method and an apparatus for automatically determining an area of a smear of test objects which is appropriate for recognition.

It is another object of the present invention to enhance the accuracy of the recognition of the test objects and enhance the number of test objects processed.

It is still another object of the present invention to a method and an apparatus for allowing the observation of an area of the same object distribution density for respective samples when different samples are sequentially processed.

In accordance with the present invention, a sample having objects smeared on a slide along a predetermined direction is observed through a microscope. In such a sample, a distribution density or a concentration of the objects, e.g. blood cells in the test sample gradually decreases from the starting point of the smear on the slide to the end point. Let us assume a case where test blood is smeared on the slide to observe the white blood corpuscles. Most of the blood cells of the blood smeared on the slide are red blood corpuscles, and the white blood corpuscles which are objects to be observed exist at a rate of only one per approximately one thousand red blood corpuscles. For a blood sample for blood cell classification, it is ideal that the smear includes the red blood corpuscles dispersed at an appropriate interval. In actual case, however, the first half area from the beginning of smear has a high distribution density and the red blood corpuscles therein are overlapped to each other or closely disposed while the latter half area has a preferable distribution density. The area of preferable distribution density depends on the conditions under which the samples are prepared and the properties of the blood, and it differs from sample to sample. What is important in the classification of blood is that the configuration of the white blood corpuscles is correctly maintained. Where the distribution density of the red blood corpuscles is high, the white blood corpuscles are collapsed by the red blood corpuscles and the configuration changes. Depending on a drying condition when the blood is smeared, the white blood corpuscles shrink in a high blood cell density area while the white blood corpuscles tend to expand or be collapsed in the area of the end of smear where the blood cell density is low.

Accordingly, it is desirable to automatically preselect an area which is best for the observation while taking the above blood cell distribution in the blood sample into consideration. This applies not only to the blood cell samples but also to cell samples such as cancer cell samples or other samples.

The present invention is based on the consideration described above, and it provides a method and apparatus for allowing the test of the test object at an optimum test area of the sample by predetermining the optimum test area of the sample when the sample such as blood cell sample is to be tested.

In accordance with the present invention, a predetermined area of a test smear on a slide is positioned within a view field of a microscope and the slide is moved from that position along the smear line on the slide, from a high density area toward a low density area, for example. As the slide is moved, the area of the smear which appears in the view field of the microscope changes. The objects to be counted, e.g. the red blood corpuscles in each area are detected by a detector to determine the densities of the objects along the movement areas on the view field of the microscope. Based on the density information, the optimum test area on the smear is determined and that area is positioned to the view field of the microscope. This completes a pre-scan mode.

In accordance with the present invention, the prescan mode may be followed by a recognition mode. In the recognition mode, the slide is moved regularly in X and Y directions and the test objects in the optimum test area are detected. When a test objects, e.g. a white blood corpuscle is detected, the slide is stopped at that position and a pattern of the test object is recognized and classified.

DETAILED DESCRIPTION OF THE PREFERRED EMBODIMENTS

Figure 1:
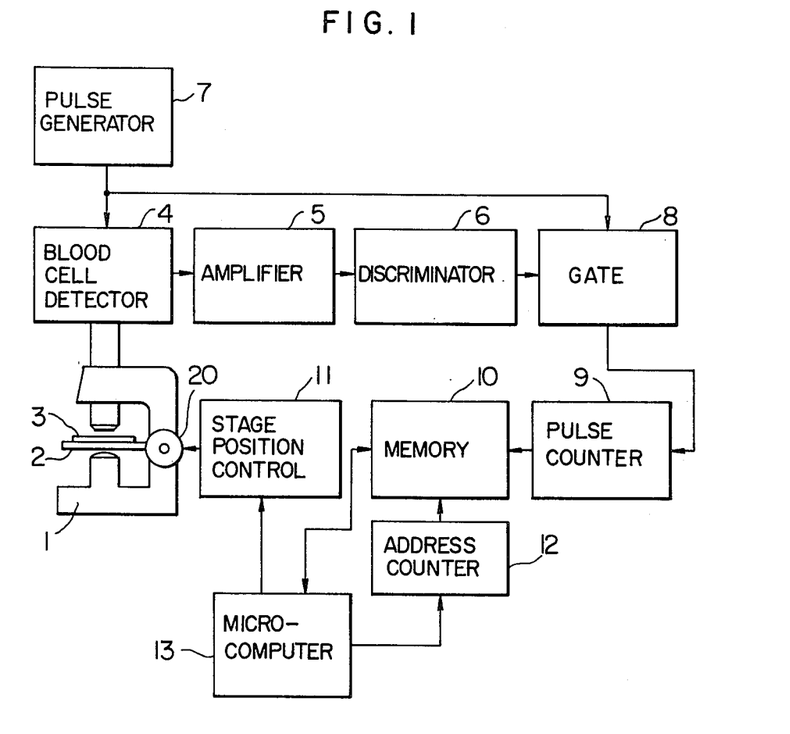
FIG. 1 shows a block diagram for illustrating one embodiment in accordance with the present invention.
Figure 3:
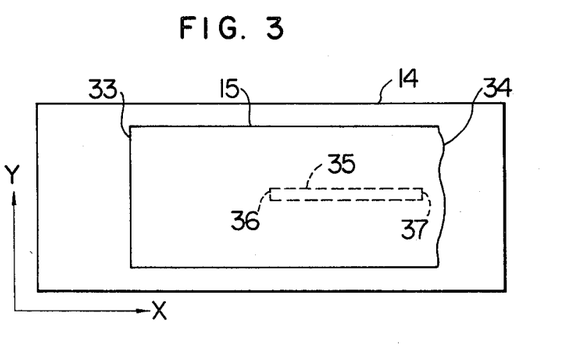
FIG. 3 shows a plan view of a slide for illustrating a smear in a pre-scan mode.

FIG. 1 shows an embodiment of an apparatus for recognizing a blood sample. In FIG. 1, an optical microscope 1 has a movable stage 2 which is movable in X and Y directions. The movable stage 2 is moved by a stage drive mechanism 20 as required to determine a particular area of the stage to be positioned to a view field of the microscope 1. Retained on the movable stage 2 is a blood sample 3 which includes, as shown in FIG. 3, a slide glass 14 and a smear 15 of test blood smeared thereon. A longer side of the rectangular slide glass 14 is referred to as an X-axis while a shorter side is referred to as a Y-axis. The slide glass 14 is held in position on the movable stage 2 such that the longer side and the shorter side of the slide glass 14 coincide with the X and Y directions, respectively, along which the movable stage 2 is moved. That is, the movable stage 2 is movable in the directions of the longer side and the shorter side of the slide glass 14.

Figure 2:
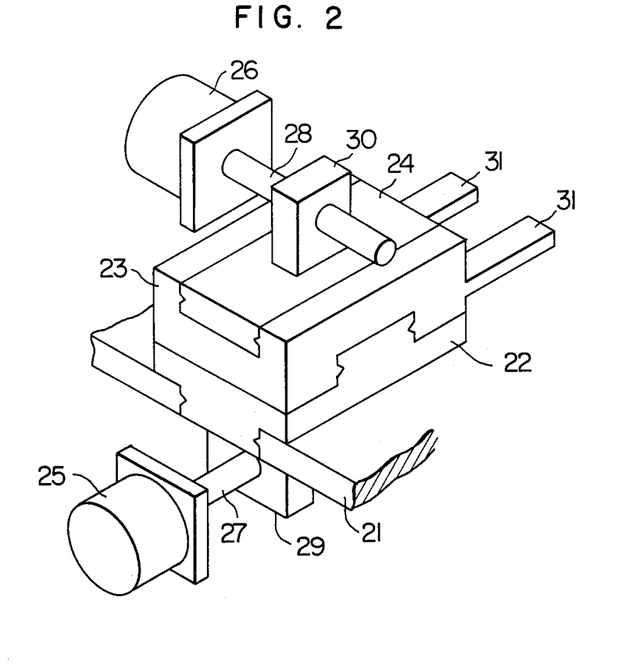
FIG. 2 shows a schematic perspective view of a stage drive mechanism shown in FIG. 1.

FIG. 2 shows a perspective view of the stage drive mechanism 20. Movable member 22 is mounted on a base 21 to allow slide movement in the Y-direction while a movable member 23 is mounted on the movable member 22 to allow slide movement in the X-direction and a movable member 24 is mounted on the movable member 23 to allow slide movement in the Y-direction. A slider 29 is fixed to the movable member 22 and a slider 30 is fixed to the movable member 24. Lead screws 27 and 28 are meshed with the sliders 29 and 30, respectively. The movable member 23 has an arm 31 on which the blood sample is held. The movable members 22, 23 and 24 and the arm 31 form the stage 2.

A Y-axis pulse motor 25 rotates the lead screw 27 to move the stage 2 in Y-direction while an X-axis pulse motor 26 rotates the lead screw 28 to move the stage 2 in X-direction.

The optical microscope 1 shown in FIG. 1 is provided with a blood cell detector 4 comprising a semi-conductor linear array, which is driven by pulse signals from a pulse generator 7. Respective channels of the semiconductor linear array comprise a plurality of semi-conductor photo-electric conversion devices arranged in series. The blood cell detector 4 detects dyed objects to be counted (e.g. red blood corpuscles in the present embodiment) in the blood sample 3.

The blood cell detector 4 is connected to a pulse amplifier 5 for amplifying a red blood corpuscle detection signal from the blood cell detector 4, thence to a discriminator 6 for producing a gate signal in response to the amplified red blood corpuscle detection signal, and thence to a gate circuit 8 which receives the gate signal.

The pulse generator 7 is connected to the gate circuit 8, which sends out the pulses only for the time duration of the red blood corpuscle detection signal. The pulses are counted by a pulse counter 9 which is connected to a memory 10 which in turn stores the total member of pulses counted by the pulse counter 9 at an address corresponding to an X-axis address on the sample 3.

A stage position control 11 controls the operation of the stage drive mechanism 20 in accordance with an instruction from a micro-computer 13. An address counter 12 specifies an address of the memory 10 in correspondence to the scanned area on the smear. The micro-computer 13 presets an optimum red blood corpuscle distribution density range and it also averages the detection results stored in the memory 10 and compares the average value with the optimum red blood corpuscle distribution density range to determine the optimum test area on the blood sample 3.

A pre-scan mode in the embodiment of FIG. 1 is now explained.

When the blood sample 3 has been mounted on the movable stage 2 by an automatic loading apparatus not shown, the movable stage 2 is moved to a predetermined position. When the view field of the microscope 1 is positioned to the center of the slide glass 14 as shown in FIG. 3, the movement of the stage 2 is stopped. Then, an object lens of the microscope is moved up and down to automatically focus the lens. Then, the slide glass 14 is moved linearly along the direction of the smear of the test blood. That is, the view field of the microscope sequentially scans the blood sample from the high red blood corpuscle concentration area to the low concentration area. In the blood samples, particularly those prepared by hard application or a wedge type automatic smear apparatus frequently used in hospitals, the blood cell distribution density, that is, the blood cell concentration gradually decreases from the beginning point of the smear on the slide glass to the end point of the smear. Most of the blood cells are red blood corpuscles, and the white blood corpuscles exist at a rate of only one per approximately one thousand red blood corpuscles. For the blood sample for the blood cell classification, it is ideal that the red blood corpuscles disperse at an appropriate interval, but in actual case the first half from the beginning of the smear includes overlapped or too closely disposed red blood corpuscles and hence has a high distribution density while the latter half area has a preferable distribution density. The preferable distribution density area depends on the conditions under which the samples are prepared and the properties of the blood and it changes from sample to sample. What is important in the blood cell classification is that the configuration of the blood cells, particularly of the white blood corpuscles is correctly maintained. Where the red blood corpuscle distribution density is high, the white blood corpuscles are collapsed by the red blood corpuscles and the configuration changes.

The movement of the stage is effected by the X-axis pulse motor 26. The stage 2 is incrementarily moved at a constant pitch of 50–500 microns. Each time the view field of the microscope is positioned at a new area on the smear, the red blood corpuscles in the view field are detected by the blood cell detector 4. The detection signal for the red blood corpuscles is applied to the amplifier 5, thence to the discriminator 6 and thence to the gate circuit 8 as the gate signal.

On the other hand, in order to drive the semiconductor linear array used in the blood cell detector 4, the pulses from the pulse generator 7 are supplied to the blood cell detector 4. The pulses from the pulse generator 7 are also supplied to the gate circuit 8 so that the pulses are counted by the pulse counter 9 only for the duration of the red blood corpuscle detection signal. Since the number of red blood corpuscles is approximately proportional to the duration of the signal detected by the blood cell detector 4, the total number of pulses counted by the pulse counter 9 corresponds to the number of red blood corpuscles detected, that is, the red blood corpuscle distribution densities in the respective view fields. The total number of pulses is stored in the memory 10 at the address corresponding to the X-axis address. In this manner, by sequentially controlling the stage position control 11, the numbers of pulses corresponding to the numbers of red blood corpuscles in the respective view fields of the microscope spaced at a constant interval on the X-axis are stored at the memory addresses specified by the address counter 12. In this manner, the stage 2 is linearly moved in the X-axis direction until the red blood corpuscle concentration in the view field of the microscope in the blood smear falls below a predetermined value, and the red blood corpuscles are detected and the counts are stored at the addresses corresponding to the respective view field addresses.

The detection results stored in the memory 10 are averaged by the micro-computer 13 and the average value is compared with an optimum red blood corpuscle distribution density (red blood corpuscle concentration) which was previously stored in the micro-computer 13. Based on the comparison, the most appropriate view field position in the measured sample is selected to determine the optimum test area by the micro-computer 13. The micro-computer 13 then specifies a start position for observation, and the stage position control 11 and the stage drive-mechanism 20 function to move the stage 2 such that the start position is positioned to the view area of the microscope.

The pre-scan mode is thus completed. Thereafter, a recognition mode starts to automatically classify the white blood corpuscles. In the present embodiment, the white blood corpuscles are recognized in the recognition mode, although the red blood corpuscles may be recognized.

FIG. 3 shows a plan view of a blood sample. The distribution of the red blood corpuscles of the blood smear 15 on the slide glass 14 is essentially uniform in the Y-axis direction except the opposite ends, but the distribution density in the X-axis direction is not uniform, that is, it gradually decreases from the beginning 33 of the smear to the end 34 of the smear. The measurement of the red blood corpuscles is effected by scanning the center area of the blood smear 15 as viewed in the Y-direction, along the X-direction. A broken line area 35 shown in FIG. 3 indicates the area of pre-scan and the start point 36 of scan is located at the center of the slide 14. The end point 37 of scan is in the low concentration area of the smear 15.

The semiconductor linear array of the blood cell detector 4 comprises a number of photo-electric devices arranged in series in the direction transverse to the direction of the smear, that is, in the Y-direction. For example, when the red blood corpuscles are to be detected by a 256-channel linear array and a microscope having an object lense of a magnification factor of 100, the number of red blood corpuscles detected in one time is sixteen assuming that the red blood corpuscle size is approximately eight microns. In the high red blood corpuscle distribution density area, the red blood corpuscles overlap or contact to each other and the correspondence between the red blood corpuscle detection signal from the blood cell detector 4 and the number of red blood corpuscles is lost.

Figure 4A:
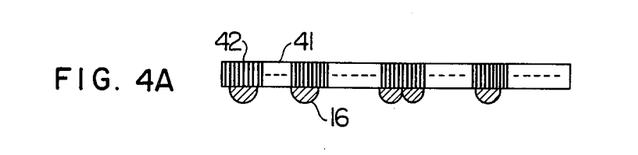
FIGS. 4A, 4B, 4C and 4D show signal status of red blood corpuscle signals detected at various points.
Figure 4B:
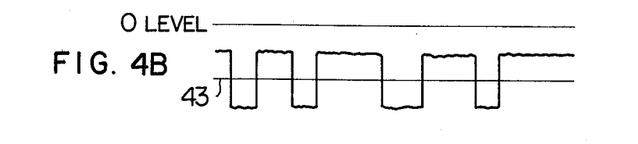
Figure 4C:
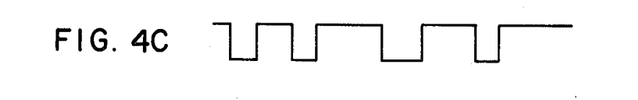
Figure 4D:
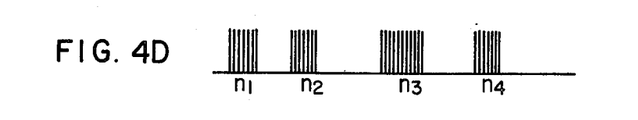

FIG. 4A diagramatically shows the correspondence between a semiconductor linear array 41 and red blood corpuscles 16. Let us assume that the patterns of the red blood corpuscles 16 shown in FIG. 4A corresponds to the number of red blood corpuscles detectable in one view field of the microscope. Photo-electric devices 42 which face the red blood corpuscles 16 produce detection signals. As a result, a signal produced by the blood cell detector 4 can be represented as a light absorption signal shown in FIG. 4B. A level line 43 in FIG. 4B shows a slice level of the discriminator 6. A reshaped signal as shown in FIG. 4C is applied to the gate circuit 8. FIG. 4D shows an input signal to the pulse counter 9.

Assuming that the width of the detection signal for each red blood corpuscle is approximately the same, a signal of double pulse width is produced when two red blood corpuscles contact to each other. Accordingly, it may be considered that the accumulation of the widths of the signals corresponds to the number of red blood corpuscles detected. This theory cannot be applied to the area where the red blood corpuscles overlap but it may be practically applied to the optimum test area where no substantial overlap of the red blood corpuscles exists. FIGS. 4C and 4D illustrate a method for converting the signal duration to a digital signal. The sum of the respective durations corresponds to the sum ($\Sigma n_i$) of the respective numbers of pulses $n_1$, $n_2$, . . . .

Figure 5A:
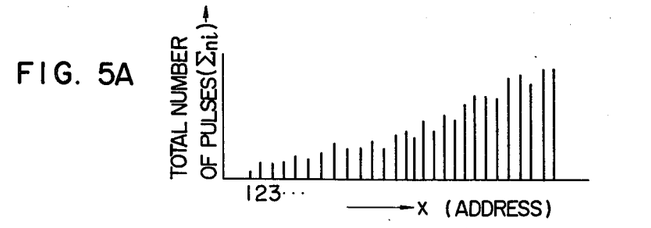
FIG. 5A shows an example of pulse distribution of the number of pulses produced in response to the X-direction movement of a blood sample.
Figure 5B:
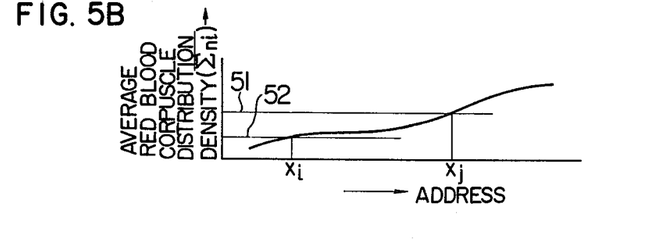
FIG. 5B shows an example of red blood corpuscle density in the X-direction of the blood sample.

FIG. 5A shows a graph of the total number $\Sigma n_i$ of pulses as the number of red blood corpuscles in the Y-axis versus the address of sample in the X-address. The measures at the respective measurement points 1, 2, 3, . . . have a large variation. Accordingly, those values are smoothened with respect to the X-axis as shown in FIG. 5B and then an optimum range $(x_i$-$x_j)$ on the X-axis is determined by a preset optimum red blood corpuscle density area for the blood cell classification, that is, a range extending from an upper limit 51 to a lower limit 52. At the start of the recognition mode, the X-axis position of the slide 14 corresponding to the upper limit 51 is positioned to the view field of the microscope. Reference values corresponding to one thousand red blood corpuscles for the upper limit of the optimum area and fifty red blood corpuscles for the lower limit, assuming that the diameter of the view field of the microscope is 200 microns, are preset in the memory of the computer 13.

Figure 6:
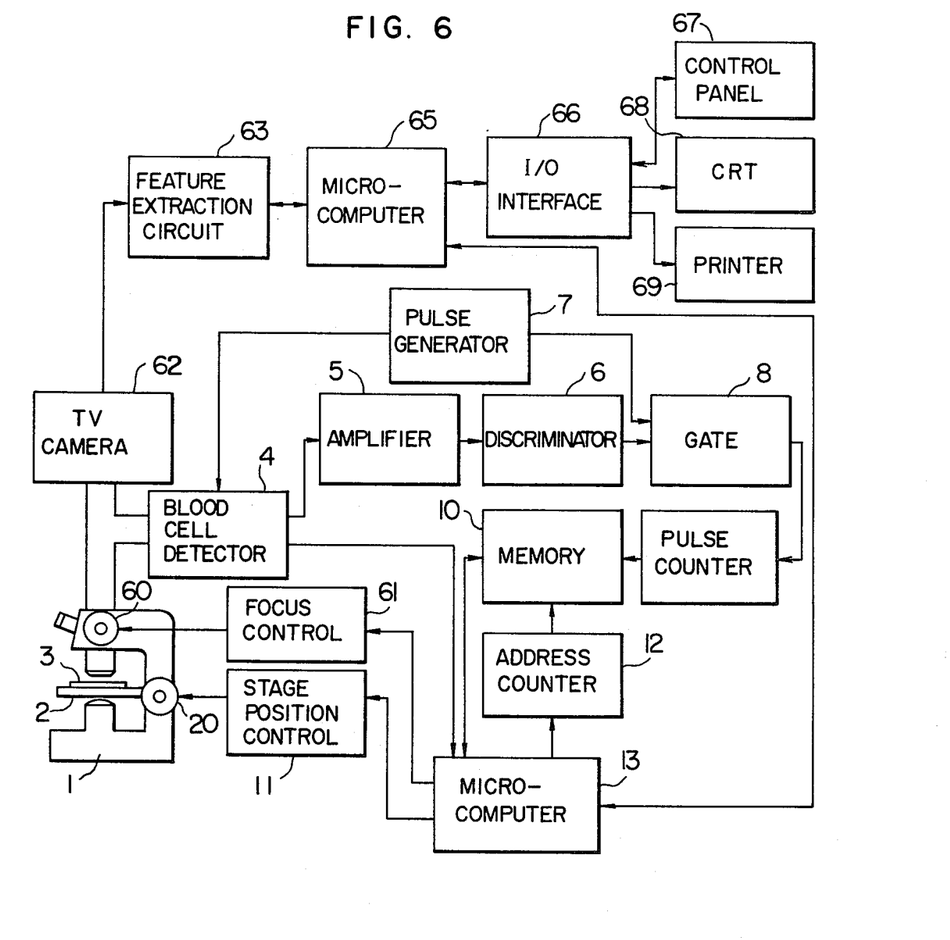
FIG. 6 shows another embodiment in accordance with the present invention.
Figure 7:
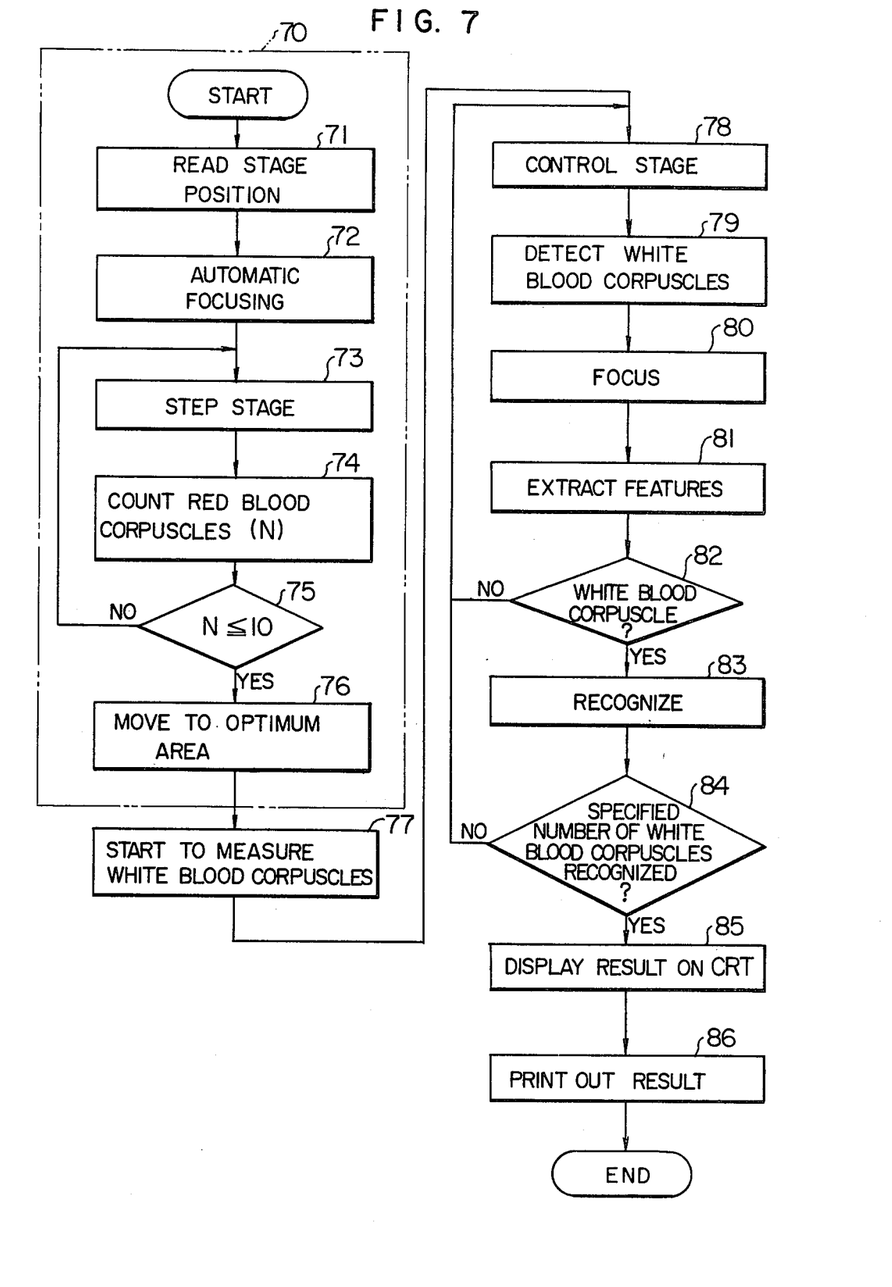
FIG. 7 shows a flow chart for illustrating the operation of the embodiment of FIG. 6.

FIG. 6 shows another embodiment of the present invention, which carries out the pre-scan mode and the recognition mode automatically. FIG. 7 shows a flow chart for the operation of FIG. 6. A chain line block 70 shown in FIG. 7 corresponds to the pre-scan mode. In FIG. 6, the elements having the same functions as those shown in the embodiment of FIG. 1 are designated by the same reference numerals.

Referring to FIG. 6, an object lens drive mechanism 60 of the microscope 1 is driven by a focus control 61 which is connected to the micro-computer 13, to move a lens cylinder upward and downward. As shown in FIG. 7, in the pre-scan mode 70, the sample 3 is mounted on the stage 2 and the stage 2 is positioned at a step 71 such that the center of the slide 3 is positioned to the view field of the microscope. Then, the focus at the center is automatically adjusted at a step 72. The stage 2 is stepped 50 microns at a time along the direction of the test smear at a step 73 and each time the stage 2 is stopped at a new view field the red blood corpuscles are counted at a step 74. So long as the count N of the red blood corpuscles is no less than ten per view field which is a stop level for the stage preset in the computer 13, the stepping operation is continued at a step 75. As the counting operation continues, the respective counts are stored in the memory 10. When the count N falls below ten which is the stage stop level below the lower limit shown in FIG. 5B, the computer determines that the specified area has been scanned and the movement of the stage in one direction is interrupted. Then, the stage 2 is moved at a step 76 such that the view field is positioned to the start point of the selected optimum test area. The pre-scan mode is thus completed and it is now ready for the recognition mode.

Referring to FIGS. 6 and 7, the operation of the recognition mode is now explained.

After the pre-scan mode has been completed, the signal from the blood cell detector 4 is sliced at a level which permits the output of only the signals corresponding to the white blood corpuscles, and the output signal is applied to the computer 13. The slice operation is carried out by a discriminator not shown. In the recognition mode, the white blood corpuscles are searched while the slide 2 is moved in the X-direction and the Y-direction alternately from the upper limit point of the optimum area on the sample to the lower limit point. At a measurement start step 77, the movement of the stage 2 is controlled at a step 78. In the course of the movement, if a white blood corpuscle is detected at a step 79, a signal from the blood cell detector 4 causes the microcomputer 13 to instruct to the stage position control 11 to move the stage 2 such that the white blood corpuscle is positioned at the center of the view field. Then, the stage 2 is stopped. The focus control 61 instantly drives the pulse motor of the drive mechanism 60 in response to the instruction from the microcomputer 13 to adjust the focus at a step 80. An image signal from a television camera 62 is processed by a feature extraction circuit 63 as shown in U.S. Pat. No. 4,175,859 to extract data necessary for blood cell classification, such as nucleus area, nucleus periphery length, nucleus concentration and cell area. When a white blood corpuscle is determined at a step 82, it is classified to one of blood cell species based on an identification algorithm stored in a micro-computer 65 at a step 83. When it is not a white blood corpuscle, the stage 2 starts to move to search a white blood corpuscle. The white blood corpuscle detection operation continues until a predetermined number of, e.g. two hundreds white blood corpuscles are detected, when the operation completes at a step 84 and the classified results are displayed on a CRT display 68 at a step 85 and also printed out on a print sheet of a printer 69 at a step 86. An I/O interface 66 of the microcomputer 65 is connected to a control panel 67 for setting measurement conditions, the CRT display 68 and the printer 69.

We claim:

1. A method for recognizing a smear comprising the steps of;
   (a) positioning a slide held on a movable stage of a microscope to a predetermined position such that the test smear on said slide is positioned within a view field of said microscope,
   (b) moving said stage along said smear in response to an instruction from a control unit such that different areas of said test smear along the length of said smear are sequentially positioned within the view field of said microscope,
   (c) sequentially detecting by a detector objects to be counted in test samples at respective measuring points appearing in the view field of said microscope as said stage is moved, to determine distribution densities of the objects to be counted at the respective measuring points,
   (d) comparing the distribution densities at the respective measuring points with a preset distribution density to determine an optimum test area on the test smear, and
   (e) moving said stage in response to an instruction from said control unit such that the view field of said microscope is positioned to said optimum test area.

2. A method for recognizing a smear according to claim 1 wherein in said step (b) a high object distribution density area of said smear is first positioned to the view field of said microscope and the measuring point is sequentially moved toward a low object distribution density area.

3. A method for recognizing a smear according to claim 1 or 2 wherein said test sample is blood smeared on said slide along a longer side of said slide.

4. A method for recognizing a smear according to claim 3 wherein said objects to be counted are red blood corpuscles and said objects to be recognized are white blood corpuscles.

5. A method for recognizing a smear according to claim 1 or 2 wherein in said step (c) pulses corresponding in number to the member of objects detected are counted.

6. A method for recognizing a smear comprising the steps of;
   (a) positioning a slide held on a movable stage of a microscope to a predetermined position such that the test smear on said slide is positioned within a view field of said microscope;
   (b) moving said stage in a predetermined direction in response to an instruction from a control unit such that different areas of said test smear along the length of said smear are sequentially positioned within the view field of said microscope;
   (c) sequentially detecting by a detector object to be counted in test samples at respective measuring points appearing in the view field of said microscope as said stage is moved to determine distribution densities of the objects to be counted at the respective measuring points;
   (d) comparing the distribution densities at the respective measuring points with a preset distribution density to determine an optimum test area on the test smear;
   (e) moving said stage in response to an instruction from said control unit such that said optimum test area is positioned within the view field of said microscope;
   (f) moving said stage such that the view field of said microscope scans transversely to the length of said smear in said optimum test area on said test smear; and
   (g) detecting said objects as the viewfield of said microscope scans and classifying the detected objects.

7. An apparatus for recognizing a smear comprising;
   an optical microscope having a movable stage for holding a slide on which a test sample to be recognized is smeared in a predetermined direction;
   means for moving said stage;

means for detecting object to be counted in measuring areas positioned within a view field of said microscope and counting said objects in the respective measuring areas;

means for storing the counts for the respective measuring areas in accordance with the moving direction of said slide; and control means for instructing said moving means to move said stage such that said slide is moved along the length of said test smear and selecting a desired one of said counts stored in said storing means to control the movement of said stage such that a start position for the recognition determined by said selected count is positioned within the view field of said microscope.

8. An apparatus for recognizing a smear according to claim 7 wherein said detecting and counting means includes a photo-electric converter of a semiconductor linear array.

9. An apparatus for recognizing a smear according to claim 7 or 8 wherein said moving means includes a motor for moving said stage in the direction of the length of said smear and in the direction transverse thereto.

10. An apparatus for recognizing a smear comprising;

an optical microscope having a movable stage for holding a slide on which a test sample to be recognized is smeared in a predetermined direction;

means for moving said stage;

means operable in a pre-scan mode for detecting objects to be counted in measuring areas positioned within a view field of said microscope and operable in a recognition mode for detecting objects to be recognized;

means for counting the objects in the respective measuring areas;

means for storing the counts for the respective measuring areas in accordance with the moving direction of said slide;

control means for instructing said moving means to move said stage such that said slide is moved along the length of said test smear and selecting a desired one of said counts stored in said storing means to control the movement of said stage such that a start position for the recognition determined by said selected count is positioned within the view field of said microscope, said control means further operable in the recognition mode to stop the movement of said stage in response to a detection signal for the object to be recognized;

means for recognizing a pattern of said object to be recognized while said stage is stopped in the recognition mode; and means for classifying the recognized objects.

* * * * *